US006589487B1

(12) United States Patent
Ly et al.

(10) Patent No.: US 6,589,487 B1
(45) Date of Patent: Jul. 8, 2003

(54) SCENT DISPENSING APPARATUS

(76) Inventors: Pao Ly, 1514 Langston St., Fort Worth, TX (US) 76105; May Vang Ly, 1514 Langston St., Fort Worth, TX (US) 76105

( * ) Notice: Subject to any disclaimer, the term of this patent is extended or adjusted under 35 U.S.C. 154(b) by 72 days.

(21) Appl. No.: 09/579,232

(22) Filed: May 30, 2000

(51) Int. Cl.[7] .................................................. A61L 2/00
(52) U.S. Cl. ........................ 422/125; 422/120; 422/122
(58) Field of Search ................................. 422/125, 122, 422/120

(56) References Cited

U.S. PATENT DOCUMENTS

| 4,937,431 A | * | 6/1990 | Jameson et al. | ............... 239/59 |
| 5,753,918 A | * | 5/1998 | Pandelisev | ............... 250/269.1 |
| 6,033,212 A | * | 3/2000 | Bonnema et al. | ............ 239/139 |

* cited by examiner

Primary Examiner—Krisanne Thornton

(57) ABSTRACT

A scent dispensing apparatus attachable to a flashlight body for heating of a liquid scent medium. The device includes a flashlight attachment having coupled thereto a heating apparatus that includes a resistive element submerged in a reservoir containing scent medium.

8 Claims, 4 Drawing Sheets

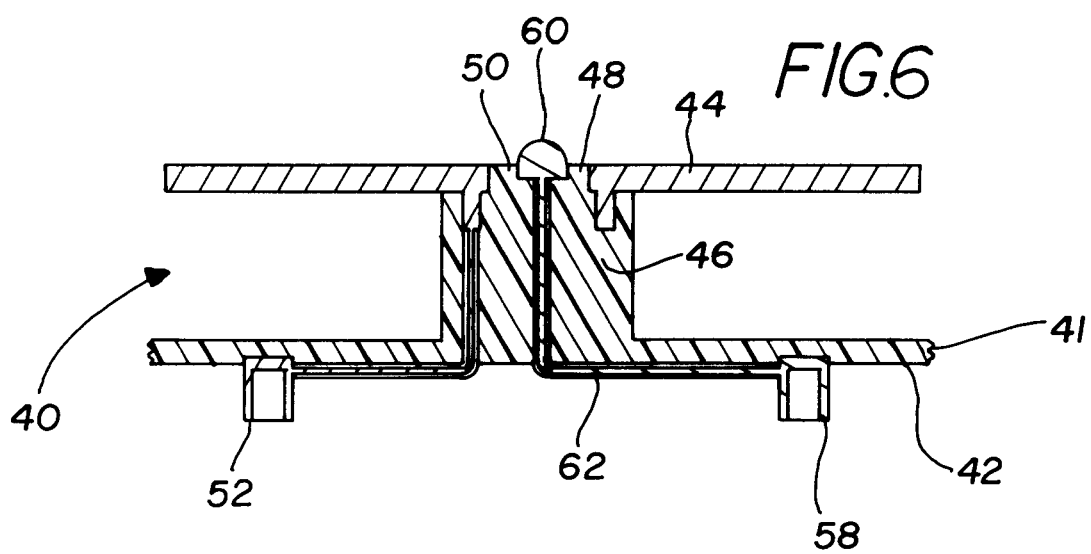

SCENT DISPENSING APPARATUS

BACKGROUND OF THE INVENTION

1. Field of the Invention

The present invention relates to scent dispensers and more particularly pertains to a new scent dispensing apparatus attachable to a flashlight body for heating of a liquid scent medium.

2. Description of the Prior Art

The use of scent dispensers is known in the prior art. More specifically, scent dispensers heretofore devised and utilized are known to consist basically of familiar, expected and obvious structural configurations, notwithstanding the myriad of designs encompassed by the crowded prior art which have been developed for the fulfillment of countless objectives and requirements.

Known prior art scent dispensers include U.S. Pat. No. 5,359,801 to Mattucci et al which discloses a scent dispenser including an upper reservoir which holds a liquid scent source and a lower chamber which houses an adjustable burner for emitting heat which in turn volatizes the liquid. U.S. Pat. No. 4,346,059 to Spector discloses an aroma-generating lamp structure having an electric bulb mounted on a base and enclosed by. a shell. A bottle filled with a liquid scent is socketed to the base and upon actuation of a pump, liquid is sprayed onto an absorbent pad disposed within the shell in the proximity of the bulb. Heat from the bulb vaporizes the liquid to generate an aroma which is exuded through vents in the shell.

While these devices fulfill their respective, particular and requirements, the aforementioned patents do not disclose a new scent dispensing apparatus. The inventive device includes a flashlight attachment having coupled thereto a heating apparatus that includes a resistive element submerged in a reservoir containing scent medium.

In these respects, the scent dispensing apparatus according to the present invention substantially departs from the conventional concepts and designs of the prior art, and in so doing provides an apparatus attachable to a flashlight body for heating of a liquid scent medium.

SUMMARY OF THE INVENTION

In view of the foregoing disadvantages inherent in the known types of scent dispensers now present in the prior art, the present invention provides a new scent dispensing apparatus construction wherein the same is attachable to a flashlight body for heating of a liquid scent medium.

The general purpose of the present invention, which will be described subsequently in greater detail, is to provide a new scent dispensing apparatus apparatus and method which has many of the advantages of the scent dispensers mentioned heretofore and many novel features that result in a new scent dispensing apparatus which is not anticipated, rendered obvious, suggested, or even implied by any of the prior art scent dispensers, either alone or in any combination thereof.

To attain this, the present invention generally comprises a flashlight attachment having coupled thereto a heating apparatus that includes a resistive element submerged in a reservoir containing scent medium.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new scent dispensing apparatus apparatus and method which has many of the advantages of the scent dispensers mentioned heretofore and many novel features that result in a new scent dispensing apparatus which is not anticipated, rendered obvious, suggested, or even implied by any of the prior art scent dispensers, either alone or in any combination thereof.

It is another object of the present invention to provide a new scent dispensing apparatus which may be easily and efficiently manufactured and marketed.

It is a further object of the present invention to provide a new scent dispensing apparatus which is of a durable and reliable construction.

An even further object of the present invention is to provide a new scent dispensing apparatus which is susceptible of a low cost of manufacture with regard to both materials and labor, and which accordingly is then susceptible of low prices of sale to the consuming public, thereby making such scent dispensing apparatus economically available to the buying public.

Still yet another object of the present invention is to provide a new scent dispensing apparatus which provides in the apparatuses and methods of the prior art some of the advantages thereof, while simultaneously overcoming some of the disadvantages normally associated therewith.

Still another object of the present invention is to provide a new scent dispensing apparatus attachable to a flashlight body for heating of a liquid scent medium.

Yet another object of the present invention is to provide a new scent dispensing apparatus which includes a flashlight attachment having coupled thereto a heating apparatus that includes a resistive element submerged in a reservoir containing scent medium.

Still yet another object of the present invention is to provide a new scent dispensing apparatus that is easily attachable to a conventional flashlight.

Even still another object of the present invention is to provide a new scent dispensing apparatus that is reusable.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 6 is a cross sectional view of the flashlight attachment of the present invention.

DESCRIPTION OF THE PREFERRED EMBODIMENT

Figure 1:
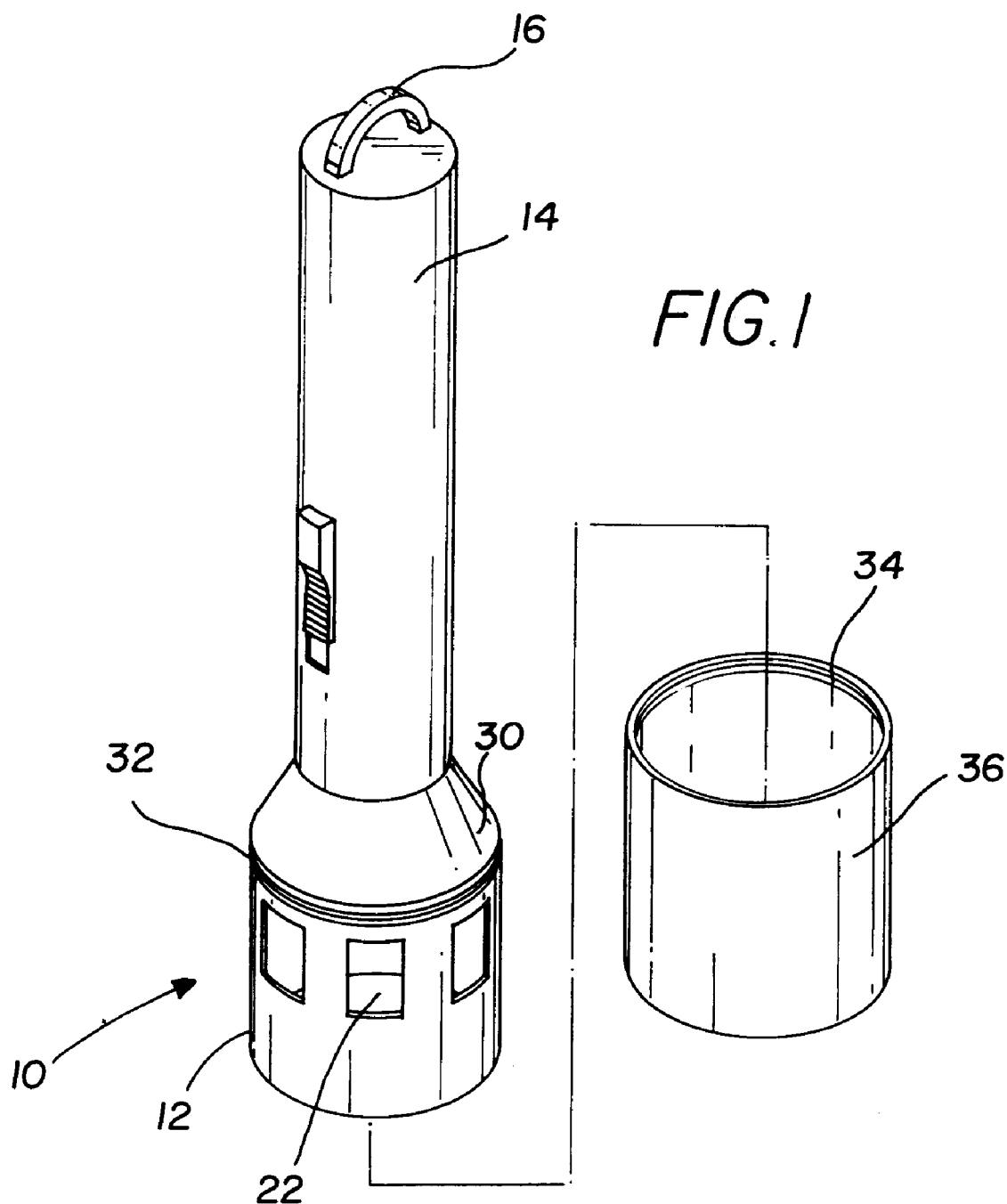
FIG. 1 is a fragmented perspective view of the present invention.

With reference now to the drawings, and in particular to FIGS. 1 through 6 thereof, a new scent dispensing apparatus embodying the principles and concepts of the present invention and generally designated by the reference numeral 10 will be described.

Figure 2:
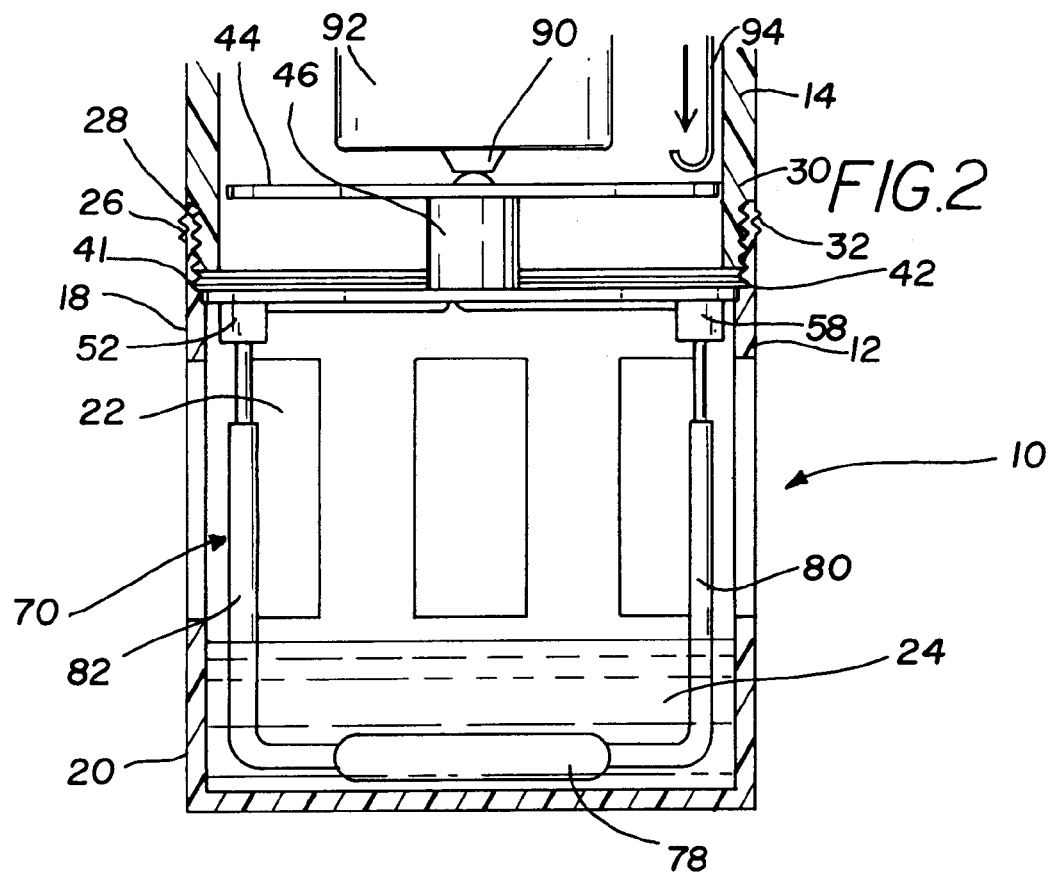
FIG. 2 is a partial cross sectional view thereof.

With reference to FIGS. 1 and 2, a first embodiment of the invention is shown including a housing 12 attachable to a conventional flashlight 14 having a loop 16 formed at one end thereof. The housing 12 is of cylindrical shape and includes an open top portion 18, a closed bottom portion 20 and a plurality of spaced apertures 22 formed around its periphery.

With particular reference to FIG. 2, the apertures 22 are formed and arranged in such manner that the closed bottom portion 20 forms a reservoir for holding a liquid scent source 24. The liquid scent source 24 may be an animal attractant, a deodorizing agent or any such volatizable liquid.

The housing 12 is attachable to a conventional flashlight 14 at its open top portion 18. A threaded portion 26 formed on the top inside periphery of the open top portion 18 is threadingly engageable to a threaded portion 28 formed at flashlight end 30. The open top portion 18 further is shown including an external threaded portion 32 for threaded engagement to a threaded portion 34 of cover 36.

Figure 3:
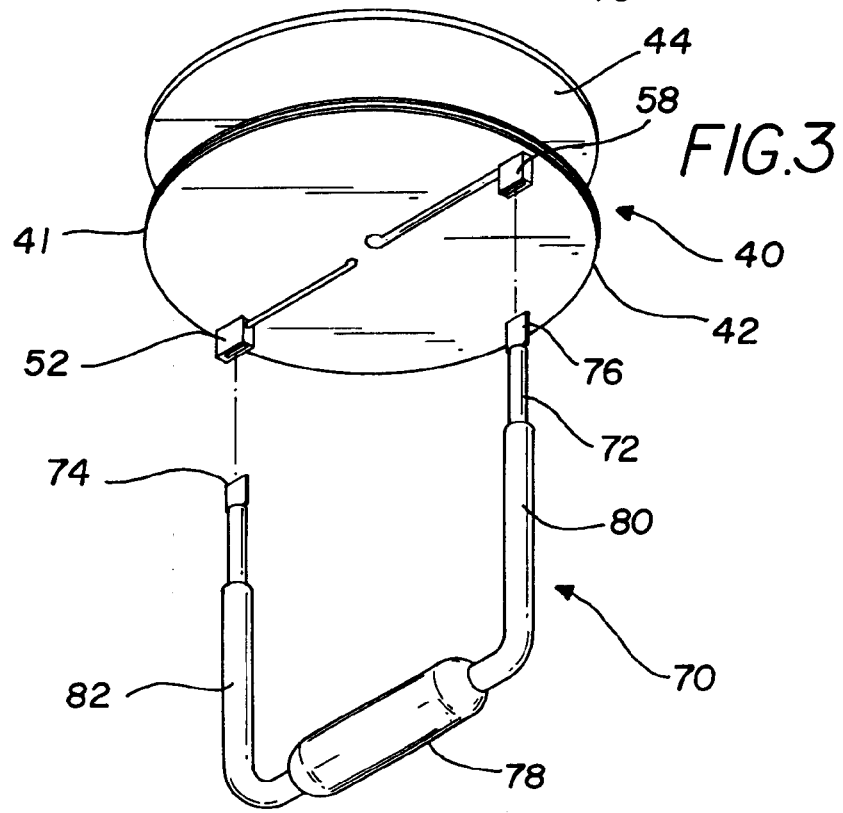
FIG. 3 is a fragmented perspective view of the heating element and flashlight attachment of the present invention.

With reference to FIGS. 2, 3 and 6, a flashlight attachment, generally designated 40, is threadingly attachable to threaded portion 26 of housing 12 by means of a threaded portion 41 formed around the periphery of a first circular plate 42. The first circular plate 42 is formed from an electrically non-conducting material such as plastic. The flashlight attachment 40 further comprises a second circular plate 44 formed in spaced relationship to the first circular plate 42 and having a smaller peripheral dimension than the first circular plate 42. With particular reference to FIG. 6, the first circular plate 42 includes an integral hub portion 46 which separates the first circular plate 42 from the second circular plate 44.

The second circular plate 44 is formed of a electrically conducting material and includes an annular opening 48 formed at a center thereof for securely receiving a top portion 50 of the hub portion, 46. The second circular plate 44 is electrically coupled to a first female, contact 52 by means of a wire 54. The first contact 52 is disposed on a lower surface of the first circular plate 42 and spaced from a second female contact 58 which is electrically coupled to a third contact 60 disposed at a center of the top portion 50 of the hub portion 46. A wire 62 couples the second contact 58 to the third contact 60.

With particular reference to FIGS. 2 and 3, a heating apparatus generally designated 70, is shown including a generally U-shaped electrical member 72 having male contacts 74 and 76 formed at respective ends thereof. The electrical member 72 includes a resistive element 78 interposed between the male contacts 74 and 76 for generating heat as is well known in the art. Insulated portions 80 and 82 extend from the resistive element 78 to positions proximate the male contacts 72 and 74.

In use, the bulb containing portion (not shown) of a flashlight 14 is removed from the flashlight 14 and the heating apparatus 70 is attached to the flashlight attachment 40. The flashlight attachment 40 is then threadingly attached to the housing 12. The reservoir of the housing 12 is filled with a volatizable medium 24 such as animal attractant or deodorant in such manner that the resistive element 78 is submerged in the medium 24 and the housing 12 is threadingly attached to the end 30 of the flashlight 14. In this configuration, the positive terminal 90 of the flashlight battery 92 is in electrical contact with the third contact 60. Upon switching the flashlight switch (not shown) on, contact 94 which is electrically connected to the negative terminal of battery 92 contacts the second circular plate 44 and an electrical circuit through the resistive element 78 is closed. The resistive element 78 in turn heats up and volatizes the medium 24. The flashlight 14 may be hung from any appropriate structure by means of loop 16.

Figure 4:
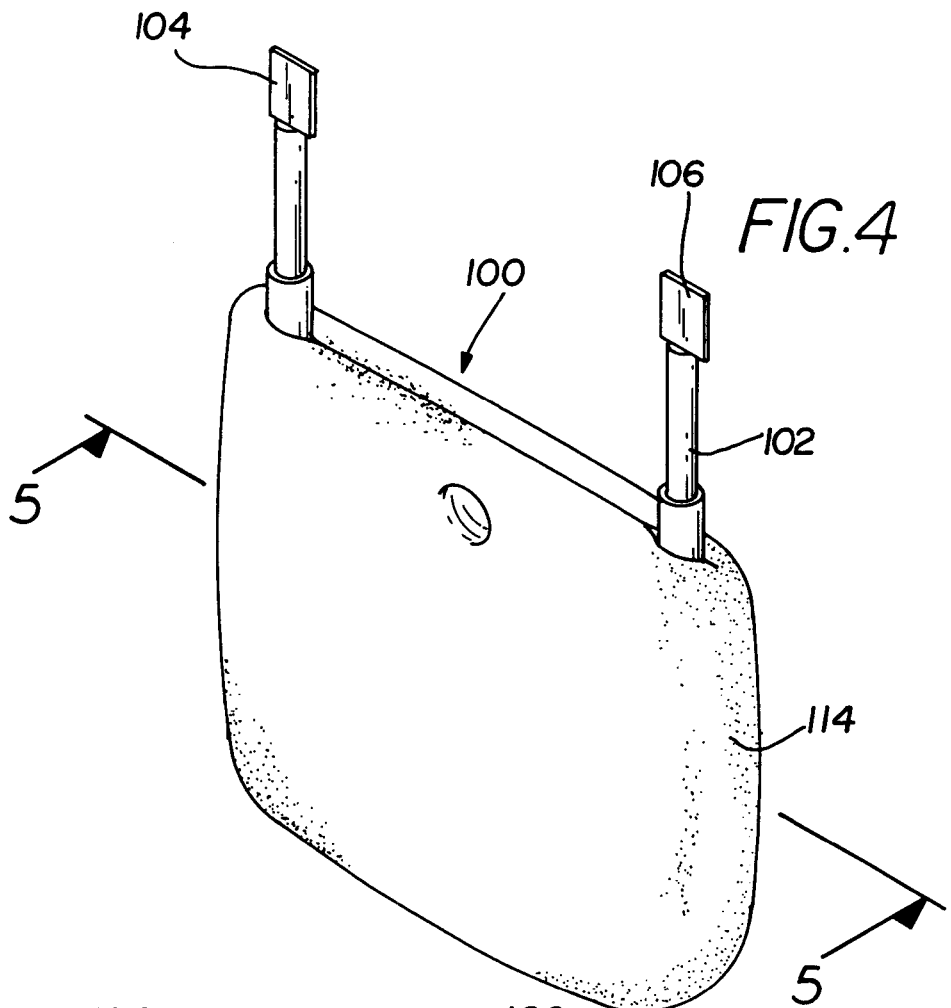
FIG. 4 is a perspective view of an alternative embodiment of the heating apparatus of the invention.
Figure 5:
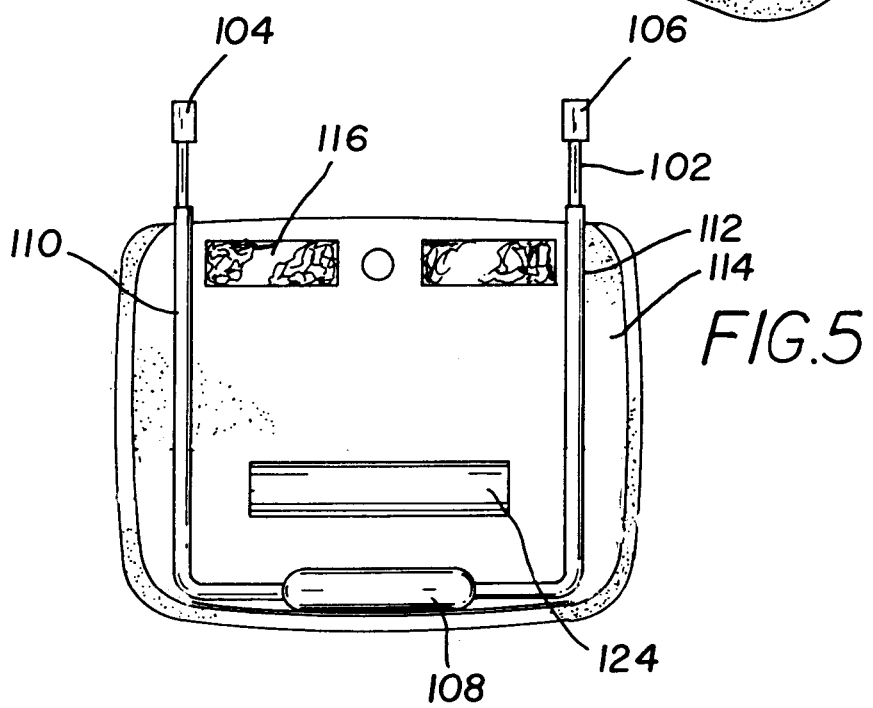
FIG. 5 is a cross sectional view taken along line 5—5 of FIG. 4.

An alternative embodiment of the heating apparatus of the invention is shown in FIGS. 4 and 5. A heating apparatus generally designated 100 includes a generally U-shaped electrical element 102 having male contacts 104 and 106 disposed at opposite ends thereof. A resistive element 108 is interposed between the male contacts 104 and 106. The electrical element 102 further includes insulated portions 110 and 112 extending from the resistive element 108 to positions proximate the male contacts 104 and 106. A fabric pouch 114, preferably formed of a porous material such as sponge, encloses a portion of the electrical member 102 and is securable therearound by means of hook and eye fasteners 116.

The fabric pouch 114 provides a medium through which a volatized scent medium may travel to exterior portions of the fabric pouch 114. In use, a scent medium container 124 is broken within the pouch 114 to allow the scent medium to come into contact with the resistive element 108. The scent medium is heated and volatized for passage through the fabric pouch 114. After the scent medium has been exhausted, the container 124 may be removed from the pouch 114 and the heating element 100 reused.

This embodiment of the invention does away with the need for the housing 12. The second circular plate 44 of the invention includes a threaded ring portion (not shown) to threadingly attach to the threaded portion 32 of the flashlight 14.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A scent dispensing apparatus attachable to a flashlight having a light bulb end removed, the apparatus comprising:

a heating means having a resistive element submerged in a scent medium; and a means for operably attaching the heating means to the light bulb end of the flashlight.

2. The scent dispensing apparatus of claim 1, wherein the resistive element is submerged in a scent medium disposed in a reservoir formed at a bottom portion of a housing, the housing being attachable to the light bulb end of the flashlight.

3. The scent dispensing apparatus of claim 1, wherein the resistive element is submerged in a porous pouch formed in surrounding relationship to the heating means.

4. The scent dispensing apparatus of claim 3, wherein the pouch is formed of a sponge material.

5. The scent dispensing apparatus of claim 1, wherein the heating means further comprises a U-shaped member having male contacts disposed at ends thereof, the resistive element being electrically disposed between the male contacts between legs of the U-shaped member.

6. The scent dispensing apparatus of claim 2, wherein the heating means is electrically attachable to a flashlight attachment, the flashlight attachment being attachable to the light bulb end of the flashlight and further comprising a first circular plate having a pair of spaced female contacts disposed upon a bottom surface thereof, the female contacts being adapted to be coupable to the positive and negative terminals of a flashlight battery.

7. The scent dispensing apparatus of claim 6, wherein the first circular plate is threadingly attachable to the housing.

8. The scent dispensing apparatus of claim 6, wherein the first circular plate is threadingly attachable to the light bulb end of the flashlight.

* * * * *